United States Patent
Ezekwe et al.

(10) Patent No.: US 10,111,448 B2
(45) Date of Patent: Oct. 30, 2018

(54) **FEED COMPOSITIONS COMPRISING *RICINODENDRON HEUDELOTII* AND METHODS OF PROCESSING AND USING THEREOF**

(71) Applicants: Michael O. Ezekwe, Vicksburg, MS (US); Samuel A. Besong, Camden, DE (US)

(72) Inventors: Michael O. Ezekwe, Vicksburg, MS (US); Samuel A. Besong, Camden, DE (US)

(73) Assignee: Alcorn State University, Lorman, MS (US)

( * ) Notice: Subject to any disclaimer, the term of this patent is extended or adjusted under 35 U.S.C. 154(b) by 0 days.

(21) Appl. No.: 15/236,424

(22) Filed: Aug. 13, 2016

(65) Prior Publication Data
US 2017/0042188 A1    Feb. 16, 2017

Related U.S. Application Data

(60) Provisional application No. 62/204,809, filed on Aug. 13, 2015.

(51) Int. Cl.
*A23K 10/30* (2016.01)
*A23K 20/147* (2016.01)
*A23K 50/30* (2016.01)
*A23K 20/142* (2016.01)
*A23K 20/174* (2016.01)
*A23K 20/158* (2016.01)
*A61K 36/47* (2006.01)

(52) U.S. Cl.
CPC ............ *A23K 10/30* (2016.05); *A23K 20/142* (2016.05); *A23K 20/147* (2016.05); *A23K 20/158* (2016.05); *A23K 20/174* (2016.05); *A23K 50/30* (2016.05); *A61K 36/47* (2013.01)

(58) Field of Classification Search
None
See application file for complete search history.

(56) References Cited

PUBLICATIONS

Agbor (J. Agric. Food Chem. (2005), vol. 53, pp. 6819-6824).*
Besong (The FASEB Journal (2010), vol. 24, No. 1, suppl.lb395).*
Leudeu (Nutrition Research (2009), vol. 29, pp. 503-509).*

* cited by examiner

*Primary Examiner* — Susan Hoffman
(74) *Attorney, Agent, or Firm* — Lawrence Arthur Schemmel

(57) ABSTRACT

The compositions, methods, and system of the invention provide increased nutrients and kidney size and reduced fat and risks of cardiovascular disease in animals by utilizing njangsa (*Ricinodendron heudelotii*) as a feed and oral supplement for the animals.

14 Claims, 2 Drawing Sheets

Figure 1. Pork sensory (taste panel): Evaluation of latissimus dorsi from pigs fed R. heudelotii meal. ªMeans, Control and treatment values did not differ (P > 0.05).

Figure 2. Oil seeds extracted from njangsa kernel.

FEED COMPOSITIONS COMPRISING *RICINODENDRON HEUDELOTII* AND METHODS OF PROCESSING AND USING THEREOF

CROSS-REFERENCE TO RELATED APPLICATION

This application claims priority from U.S. Provisional Patent Application Ser. No. 62/204,809 filed Aug. 13, 2015. The entirety of that provisional application is incorporated herein by reference.

FIELD OF THE INVENTION

This invention relates to the field of feed and food compositions that include *Ricinodendron heudelotii* and more specifically to processes and methods of processing and using *R. heudelotii* in animal feed compositions and oral supplements to increase animal intake of omega-3 fatty acids and nutrients and to reduce fat and increase kidney size in the animal and thereby reduce the risks of cardiovascular diseases in animals and humans and improve animal meat quality.

BACKGROUND OF THE INVENTION

Njangsa (*Ricinodendron heudelotii*) is a tropical tree that grows in the forest of West and Central Africa and produces fruits that are manually shelled to collect oil seeds and dried. A compositional analysis of njangsa revealed a unique nutrient presence of long chain omega-3 fatty acids not usually associated with plant materials. The seed had 31.4% crude protein and 44.7% lipid. Of this lipid, about 73% was composed of polyunsaturated fatty acids (PUFA), almost entirely of eicosapentaenoic acid, with about 18% oleic acid. Preliminary studies were conducted to determine if njangsa seed meal would alter the lipid and other metabolite levels in pigs and/or improve pork quality traits. Twelve (12) crossbred gilts and barrows were fed corn-soybean diets containing 14% crude protein. A treatment group was supplemented with a dietary composition comprising at least about 2% njangsa oil seed meal. Growth and carcass traits showed similar carcass characteristics (P>0.05). Backfat measurement was reduced (P<0.05), while kidney weight was elevated (P<0.01) in treated animals. Pork sensory evaluations were not different between the experimental groups. An oil-rich supply of long chain PUFA from sources other than seafood, such as the present invention, provides a more sustainable source.

There exists a need to provide compositions and processes for obtaining such compositions and for processes for administering to animals to increase animal intake of an oil-rich supply of long chain polyunsaturated fatty acids from sources other than seafood. The present invention provides such compositions and processes and methods for increasing animal intake of omega-3 fatty acids and nutrients and in reducing fat in animals and in reducing the risks of cardiovascular diseases in animals, including swine, poultry, livestock, and/or humans, for example, as well as improving animal meat quality.

SUMMARY OF THE INVENTION

The present invention provides novel feed compositions comprising *Ricinodendron heudelotii* (njangsa) wherein the njangsa fruit and/or its seed extract, specifically the oil seeds, has been harvested from the njangsa tree. The invention provides processes and methods of processing and of using the njnagsa seed to increase animal intake of omega-3 fatty acids and intake of nutrients and to thereby increase animal kidney size and reduce animal fat and the risks of cardiovascular diseases in animals, including swine, poultry, livestock, and/or humans, for example, and to improve animal meat quality using the feed compositions through dietary feeds and feed supplements, as well as through pressed tablet, tablet, paste, pill, gel, encapsulated capsule, liquid, suspension, and/or powder or loose powder forms, or a combination thereof, for example. Additionally, the compositions of the invention provide an oil-rich supply of long chain polyunsaturated fatty acids and nutrients including antioxidants to the animal fed with the compositions, thereby enhancing animal health.

With the foregoing and other objects, features, and advantages of the present invention that will become apparent, the nature of the invention may be more clearly understood by the following detailed description of the preferred embodiments of the invention and by the appended claims.

BRIEF DESCRIPTION OF THE DRAWINGS

These drawings accompany the detailed description of the invention and are intended to illustrate further the invention and its advantages. The drawings, which are incorporated in and form a portion of the specification, illustrate certain preferred embodiments of the invention and, together with the entire specification, are meant to explain preferred embodiments of the present invention to those skilled in the art.

DETAILED DESCRIPTION OF THE INVENTION

Figure 1:
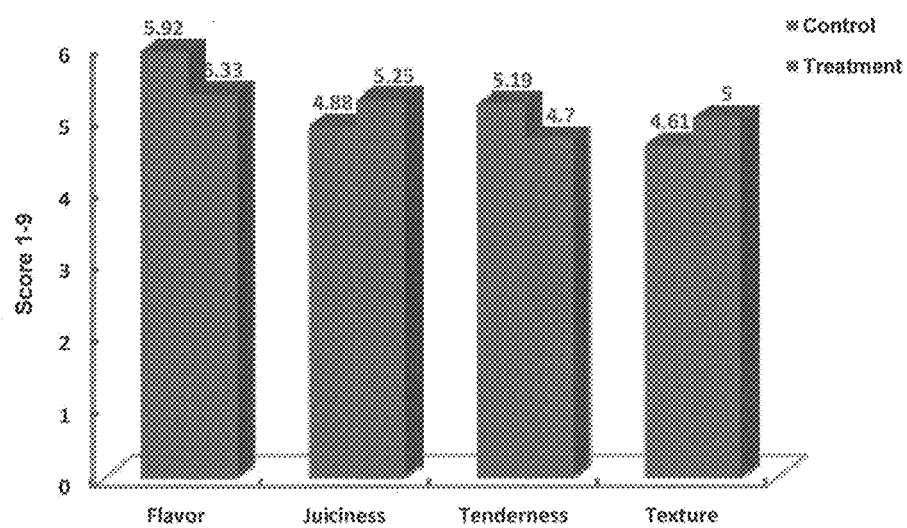
FIG. 1 is a graphical illustration of pork sensory (taste panel) and the evaluation of latissimus dorsi from pigs fed *R. heudelotii* meal.

The present invention provides a method, system, process, and compositions that utilize njangsa (*Ricinodendron heudelotii*) as an oral dietary and/or supplemental composition for animals, including humans, via the diet and/or water supply to enhance animal health and intake of long-chain omega-3 fatty acids and resultant biological effects and benefits. Animals to benefit from the invention include monogastric animals such as swine, grazing animals, poultry, livestock, and humans, for example. Additionally, the invention applies to the utilization of njangsa in enhancing human health, as the additional source of such nutrients can potentially benefit humans both directly and indirectly through consumption of treated animals such as swine, poultry, and livestock, for example.

The compositions and methodology of the invention provide for improving the nutritional supplementation and nutritional supplementation profile of, for, or in an animal in need and for reducing fat, particularly back fat, in the animal and the risks of cardiovascular diseases. The invention provides for forming at least one oral composition using at least one delivery media combined with njangsa and/or njangsa seed extract, which is obtained from the njangsa seed, and for feeding and/or administering the composition, actively, passively, or both, to an animal in need in an effective amount and for a suitable amount or period of time, such that the effective amount improves or enhances the nutritional supplementation, and/or the nutritional supplementation profile, of or in the animal and reduces fat (back fat) in the animal, increases the kidney size in the animal, and/or reduces the risks of cardiovascular disease in the animal. The composition typically and preferentially contains at least one delivery media and at least about 2 percent by weight of njangsa seeds, njangsa seed extract, or a combination thereof, and mixed with meal diet. The seeds are obtained from mature njangsa tree fruit. The delivery media can be an orally ingestible solid, liquid, or a combination thereof. Moreover, the feed composition may be comprised of njangsa and/or njangsa seed extract and meal diet comprised of protein, or crude protein, which can be from corn, soy, soybean, and the like, or any combination. The invention utilizes njangsa comprising seeds and/or seed extract that is preferentially dried, lyophilized, and ground prior to mixing or combining with at least one delivery media, such as meal diet and the like. The delivery media can typically be an orally ingestible solid, liquid, or a combination thereof. In application, the compositions and methods of the invention can typically be provided and utilized via feed (mixed in) and/or meal diet. The compositions of the invention may be in the form of or delivered via dietary feeds and feed supplements, as well as through pressed tablet, tablet, paste, pill, gel, encapsulated capsule, liquid, suspension, and/or powder or loose powder forms, or a combination thereof, for example.

The methodology of the invention includes utilizing the compositions of the invention as dry, liquid, and/or water-based supplements, or a combination thereof. The compositions and methodology of the invention may consist of an animal feed, drink, dairy product, juice, soup, human food, or any combination thereof, for example. Administration of the compositions to the animal in need can be by feeding the animal, either passively or actively, via a delivery media that is an orally ingestible solid or liquid, or some suitable combination.

Introduction

*Ricinodendron heudelotii*, commonly known as njangsa, is a fast growing, late secondary tropical tree found in the Guinean-Congolean humid forest of west and central Africa. *R. heudelotii* reaches maturity between about 4 to 5 years before producing fruits. The fruits are usually manually shelled to collect the oil seeds. The njangsa seed is extracted from the hard shell through a crude process which involves boiling the kernel for hours at high temperature above 100° C. This process subjects the kernel to a high temperature which often results in oxidation and rancidity of the oil. The seed is valued for its distinctive flavor. The seeds are dried, ground, and used for soup and as an ingredient for seasoning baked meats and fish, and as a flavoring and thickening agent in food (Plenderleith, 1997). The oil seed is an economical and valuable agricultural plant, especially in Cameroon. *R. heudelotii* is a source of many nutrients and biologically-active compounds including omega-3 fatty acids, essential amino acids, minerals, and antioxidant vitamins (Besong et al., 2010).

Njangsa oil seed is widely used in West Africa as food and has medicinal as well as industrial applications (Mori et al., 1999; Orwa et al., 2009; and Ekam, 2003). The leaves are used as an important source of high-quality fodder for sheep and goats in the dry season. It was discovered that the green foliage had average crude protein content of 16% and without any known toxicity (Anigbogo, 1996; Latham, 1999). However, the presence of unnamed traces of an alkaloid and resin was reported to be contained in the seed (The World Agroforestry Centre (ICRAF), 1999). Manga et al., (1999) reported that total fat content of *R. heudelotii* kernels from various locations in the Cameroons ranged from 50 to 65.2%. This compared favorably with the oil content of commercial vegetable oils reported by Zambiazi (2007). Fatty acid composition showed a high level of polyunsaturated fatty acids (PUFA) ($C_{18-3}$) and essential amino acids (Tehiegang et al. 1997). Crude protein levels ranged from 49.9 to 65.2% (Manga et al., 2000).

The presence of longer chain omega-3 fatty acids in *R. heudelotii* oil seeds creates a greater need for exploitation of this plant for human and animal nutrition. There is an increasing trend towards producing leaner pork from dietary or genetic improvement methods by altering the fatty acid profile resulting in healthier market products. This trend has resulted in producing pork with reduced subcutaneous fat and an ideal amount of intramuscular lipids. Previous studies have shown that these desired qualities may be accomplished by low protein diets (Doran et al., 2006). Patents for enriching lean meat with omega-3 fatty acids exist, which create a future possibility for meat providing appreciable quantities of these fatty acids. Omega-3 fatty enriched lean meat has the potential to expand the feed industry's market for omega-3 enriched rations (Nettleton, 1995). The objectives of the studies that resulted in the present invention were to determine the nutritive composition of njangsa oil seed and its effect on lipid and other metabolites in animals, specifically pigs, fed supplements of the oil seed meal. Meat quality and carcass traits including shelf life of meat from njangsa fed animals were determined.

Materials and Methods

Sixty kilograms of dried njangsa seeds were purchased from limited resource farmers in the Western Region of Cameroon, West Africa. Extracted seeds were dried and kept at room temperature and later placed in Ziploc bags prior to shipment to the United States. Upon receipt in the inventors' lab, the seeds were stored at about 4° C. The seeds were blended and mixed to yield oil and seed meal. The dried seeds were "full fat" seeds, lyophilized, and ground prior to mixing into rations. Two feed samples were analyzed for nutrient composition (Covance Lab Inc., Madison, Wis.). Seed extract of njangsa seeds obtained from mature njangsa tree fruit can alternatively be utilized in the feed composition. The feed composition can likewise be processed into multiple forms for feeding to animals and/or humans including, but not limited to, pressed tablets, powder, loose powder, pills, gel, encapsulated capsules, liquid, suspension, or any combination of such forms.

Previous studies have shown that *R. heudelotii* oil seed meal did not store long chain omega fatty acids (Tchankou Leudeu et at, 2009). The failure to detect poly-unsaturated omega-3 fatty acids in njangsa oil seed may be due to regional variations, processing, and/or methods of oilseed extraction. More recent studies by Ogunka-Nnoka did not report any presence of omega-3 PUFA acids in njangsa oil extracts.

However, processing methods are critical in producing the right and effective quality of njangsa oil meal. The particular processing methods of the invention in fact retain the long chain omega-3 fatty acids within the njangsa seed and seed extract, which results in the positive biological effects upon consumption by the animals of the njangsa compositions that were observed by the inventors. For the invention, the njangsa seed is extracted from the hard shell through a crude process which involves boiling the kernel for long hours at a high temperature which is above about 100° C. This crude process subjects the kernel to a high temperature which often results in oxidation of PUFA acids and rancidity of the oils. This process is essential and, if critically followed, will yield and preserve the quality of njangsa oil seed. For the invention, the use of low-cost shelling equipment, steel Nutcracker for peeling off the hard shell was used to extract the oil seeds. The oil seed was then lyophilized after extraction until ration formulation to preserve the composition of the njangsa.

The invention provides a novel approach to developing an animal and particularly swine feed comprising *R. heudelotii* seed extracts having an intake of omega-3 fatty acids (PUFA) capable of reducing fat in animals and improving animal meat quality. Studies suggest that omega-3 fatty acids reduce cardiovascular disease and/or risk factors through decreased risks for arrhythmias and thrombosis, decrease of triglyceride and remnant lipoprotein levels, decrease the rate of growth of atherosclerotic plaque, improve endothelial function, lower blood pressure, and reduce inflammatory responses. EPA and DHA are both essential building blocks for tissue structures and important biological mediators in health and disease by regulating metabolic pathways. The amount of about 2 percent njangsa in the feed composition diet was the minimum amount or level that elicited animal response. Higher dosages of njangsa may likely enhance the effect of biological responses in animals that may be achieved.

Diet and Experimental Design

Twelve crossbred gilts (163.3 kg) were obtained and housed at Alcorn State University Swine Research and Development farm. The animal experimental protocols were reviewed and approved by Alcorn State University Animal Care Committee. These pigs were randomized according to body weight and placed into two groups and housed at separated pens. The two groups were allotted into either the control or the njangsa-fed groups. Pigs were fed about 14% crude protein from a corn-soybean meal diet supplemented with either about 2% njangsa meal (treatment group n=6 per group) or control diet (no njangsa) group (n=6 per replicate) and formulated to meet the nutrient requirement for finishing pigs (NRC, 1988). Diets were fed ad libitum and feed intake was calculated on a weekly basis. All diets were isocaloric and isonitrogenous (Table 1). A two-week acclimation period was followed before the six weeks experimental treatment. Weekly body weight and blood samples were collected for analysis of total cholesterol and triglycerides. All pigs were slaughtered at the end of the experiment at the USDA Meat Inspection Facility. Liver, kidneys, and gastronemius muscles were dissected and weighed.

Analytical Methods of Njangsa Seeds, Blood and Animal Tissues

Five grams of ground samples were taken for crude protein and total ash extractions (Association of Analytical Communities (AOAC), 1995). Total lipids were determined by the one-step methylation method (Sukhija and Palmquist, 1988) using hexane as a solvent. Fatty acid and amino acid compositions were determined by gas chromatographic and high performance liquid chromatography (HPLC) techniques, respectively (Midwest Laboratories, Omaha, Nebr.). Vitamins A and ∝-tocopherols in pork muscles (gastronemius) and feed were analyzed by Convance Laboratories (Madison, Wis.).

Analysis of Blood and Animal Tissue

Serum cholesterol and triglycerides were analyzed using Wako Diagnostics kits (Wako Diagnostics, Richmond, Va.). Total lipids and cholesterol in skeletal muscles, liver tissues, and triglycerides were extracted and quantified (AOAC, 1998).

Statistical Analysis

Data was analyzed statistically using Statistix-7 for Windows, Analytical Software 2002. Body weight, daily gain, feed intake, and efficiency (gain/feed) were analyzed as six (6) experimental units per treatment using Statistix-7 for Windows, Analytical Software 2002. A 2×6 factorial analysis of variance was used to determine the effect of diet treatment and bleeding times on blood metabolites and lipid levels. Treatment means were separated by the least significant difference (LSD) technique.

Results and Discussion

The chemical composition of njangsa seed meal showed a remarkable nutritive quality previously not reported from plant sources (Table 2). The crude protein content compares well with other well-known oil seeds, such as peanut and soybean meals. Plant protein sources were reported to enhance the hypocholesterolemic effects of dietary polyunsaturated fatty acids (Forsythie et al., 1980). The unique lipid composition of njangsa is remarkably different from others reported for plants. The inventors of the present invention discovered that njangsa oil seeds (*R. heudelotii*) (FIG. 2) have high levels of polyunsaturated fatty acids and are rich in substantial amounts omega-3 fatty acids, especially eicosapentaenoic acid (EPA), not found in other oil seed meals (Table 3). EPA and docosahexaenoic acid (DHA) are usually associated with marine fish oils and have not been reported in plant species at high concentrations observed in the studies that resulted in the present invention (Table 3). The inventors' results showed that njangsa oil is a potential alternative to fish oil and is a promising land-based source for omega-3 fatty acids, in contrast to the findings of Tchankou Leudeu et al., (2009). The differences may be due to the differences in processing and sensitivity of the analytical methods used. Njangsa oil appears to be superior to all commercial vegetable oils that are used for cooking (Table 3). Previous chemical composition analysis indicated crude protein ranges of 49.9% to 65.2% and 49.3% to 63.5% fat in forty-seven (47) collections of njangsa seeds from different regions in Cameroon (Manga et al., 1999). These results are in agreement with those reported in the present studies. However, the presence of the high amount of PUFA was not expected. The identification of EPA and DHA for the first time in significant amounts in njangsa oil seed and the use of the composition in feeding to animals to reduce fat and the risks of cardiovascular disease and to improve animal meat quality and health and meat shelf life can result in beneficial and positive effects on animal and human health and nutrition. EPA supports cardiovascular, immune, and other systems and is important to human health (Pakala et al., 1999). Linolenic acid in most instances must be converted to long chain unsaturated omega-3 fatty acids such as EPA & DHA before it can be metabolically useful to humans and animals (Nettleton, 1965). Omega-3 fatty acids are taken up by many cells and tissues of animals, including plasma, liver, lung, kidney and spleen, aorta, vascular endothelium, heart, and tumors. Fatty acids, particularly DHA, are concentrated in the membrane phospholipids of the retina and brain, while EPA is preferentially distributed in liver, kidney, platelets and blood cells (Nettleton, 1995). Pigs in the njangsa diet had a significant (P<0.01) increase in kidney size with no prior adverse health problems. However, it was difficult to determine the cause of the differences in kidney size from the studies. The inventors' results suggest that incorporation of njangsa seeds in the diet would provide a good source of omega-3 fatty acids which are lacking in the Western diet. The American Heart Association (AHA) and National Academy of Sciences and Institute of Medicine have recently made dietary recommendations focusing on substituting eicosapentaenoic (EPA) and docosahexanoic acids (DHA) for saturated fatty acids.

Table 4 presents data on the amino acid content of njangsa oil seed. While low in lysine and tryptophan, the percentage of essential amino acids to total amino acids was 40.59%, which was higher than normal values for a well-balanced protein feed (Tehiegang et al., 1998). Njangsa oil seed had a good balance and concentration of other essential amino acids. In view of the spread of this tropical tree in west and central Africa, the importance of developing the production of the seeds as a sustainable source of omega-3 fatty acids for animals and human consumption cannot be overemphasized. Strategies for the domestication of R. heudelotii have been suggested (Ngo Mpeck et al., 2003).

Carcass composition data in pigs are presented in Table 5. There was a significant reduction (P<0.05) in back fat of pigs supplemented with 2% R. heudelotii meal. No significant differences were observed in other carcass measurements. Furthermore, it is noteworthy that no visible lesions were observed among the organs and tissues of the carcasses. Liver, muscle, and serum studied did not show improved storage of polyunsaturated fatty acids (EPA & DHA) or a reduction in cholesterol and triglycerides (data not presented). Stewart et al. (2001) observed that a diet containing modified pork with high polyunsaturated fatty acids (PUFA) significantly lowered total plasma and LDL-cholesterol in women, thus suggesting a new approach for lowering the consumption of saturated fat and improve the quality of pork products. Other studies showed that freeze-dried purslane leaves containing high levels of omega-3 fatty acids reduced blood total cholesterol, and LDL-cholesterol in humans and pigs (Besong et al., 2011). It is not clear why R. heudelotii oil seed meal fed to pigs did not influence tissue lipids in the present study. The level of PUFA supplied by R. heudelotii (2% of total diet) might have been completely metabolized by the impacted organs and tissues (kidney and adipose tissue), and not much was left to influence other tissues. Reports have shown that substitution of 15% lipids in diets with PUFA concentrate prevented fat accumulation with preferential reductions in abdominal fat depot in mice (Ruzickova et al. (2004); Flachs et al., (2005). These studies led to the suggestion that reduction in both hyperplasia of adipose tissue cells and hypertrophy of adiposities contribute to reduced accumulation of body fat as a result of PUFA intake (Kopesky et al., 2009), agreeing with the results of the present studies.

Figure 2:
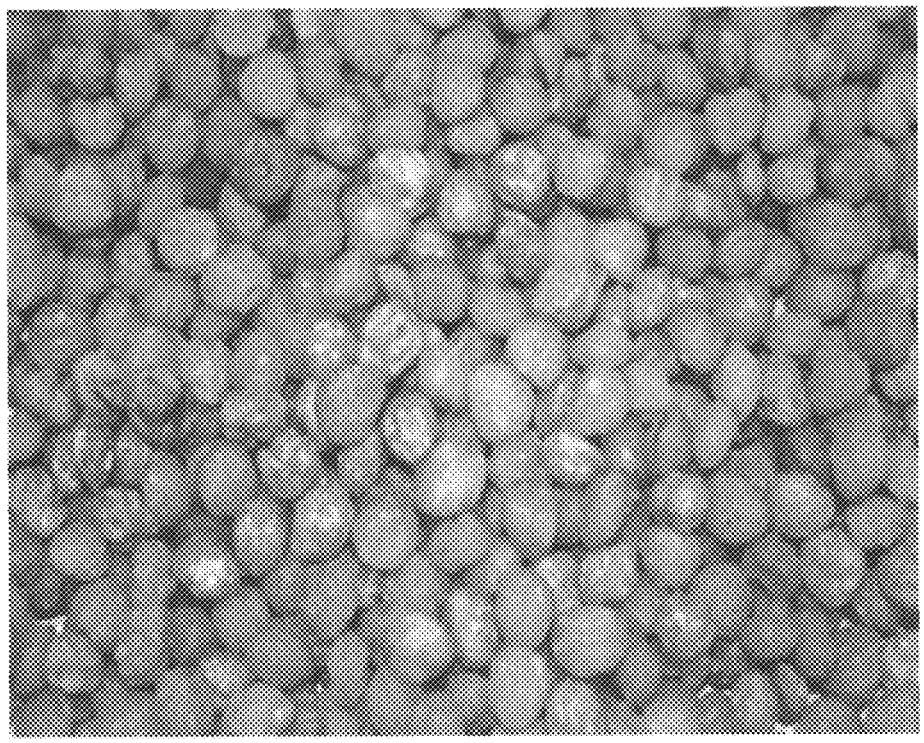
FIG. 2 is a pictorial representation of oil seeds extracted from the njangsa kernel.

The sensory evaluation of pork from treated and control animals did not show any significant (P>0.05) differences in flavor, juiciness, tenderness, and texture. FIG. 1 shows a graphical illustration of pork sensory (taste panel) and the evaluation of latissimus dorsi from pigs fed njangsa meal. Addition of the PUFA-rich diet used in the present studies that resulted in the present invention did not adversely affect the quality of pork. It appears that the higher level of antioxidant vitamins present in njangsa seed meal (Table 6) contributed to the improvement in pork's nutritional quality. FIG. 2 shows a representation of oil seeds extracted from the njangsa kernel. High levels of vitamin A in meat after long term storage may have contributed to enhanced shelf life in meats from treated animals (Table 6). An almost two-fold (P<0-05) increase in the vitamin A level in the meat of animals fed with njangsa feed meal indicates efficient absorption and storage from feed sources by pigs.

CONCLUSION

The quantity and quality of polyunsaturated fatty acids (PUFA) in R. heudelotii seeds indicate an unusual presence of EPA in plant species, suggesting a potential land-based source of omega-3 fatty acids. The presence of high amounts of vitamins A and E in njangsa seed provides a potential source of dietary antioxidant nutrients and may also provide a protective effect on PUPA in the seed. The studies that resulted in the present invention show that incorporating R. heudelotii oil seed meal into animal and swine diet significantly reduced back-fat thickness by about 31.1% and an elevated kidney weight by about 20.8%. High levels of antioxidant vitamins reflected in the meat after long term storage indicate a possible improvement in shelf-life of meat of animals fed with njangsa oil seed. Consumers will likely benefit from food/meat products enriched with minerals and antioxidant vitamins and PUFA from R. heudelotii for both animal and human nutrition. Results from the swine feeding trials utilizing njangsa oil seed show a shift in fat deposition toward a reduction in back-fat and elevated vitamin A and increased vitamin E concentrations in meats. The methods of use of the njangsa composition show that great potential exists for the use of R. heudelotii oil seeds for meat quality improvements, reduction in fat and the risks of cardiovascular diseases, and enhancement of animal and human health and nutrition.

The above detailed description is presented to enable any person skilled in the art to make and use the invention. Specific details have been revealed to provide a comprehensive understanding of the present invention, and are used for explanation of the information provided. These specific details, however, are not required to practice the invention, as is apparent to one skilled in the art. Descriptions of specific applications, analyses, results, and calculations are meant to serve only as representative examples. Various modifications to the preferred embodiments may be readily apparent to one skilled in the art, and the general principles defined herein may be applicable to other embodiments and applications while still remaining within the scope of the invention. There is no intention for the present invention to be limited to the embodiments shown and the invention is to be accorded the widest possible scope consistent with the principles and features disclosed herein.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above-described exemplary embodiments.

Moreover, the compositions, methods, processes and uses of the present invention, like related compositions, methods, processes and uses used in the feed composition and processing and production arts, are complex in nature and are often best practiced by empirically determining the appropriate values of the operating parameters and/or by conducting computer simulations to arrive at best design for a given application. Accordingly, all suitable modifications, combinations, and equivalents should be considered as falling within the spirit and scope of the invention. The present invention is sufficiently flexible and configurable such that it may be utilized in ways other than those shown.

TABLE 1

Swine finisher diet composition (CP 14%) fed to growing pigs.

| Ingredient (%) | Experimental treatment | |
|---|---|---|
| | Control | Njangsa |
| Corn | 83.79 | 82.42 |
| Soybean | 12.2 | 12.46 |
| Njangsa | — | 2.0 |
| Tallow | 1.89 | 1 |
| VitaminPremix[a] | 0.25 | 0.25 |
| Salt | 0.25 | 0.25 |
| Dical $PO_4$ | 0.71 | 0.71 |
| Limestone | 0.9 | 0.9 |
| Antibiotics | 0.01 | 0.01 |
| Total | 100 | 100 |
| ME (Kcal/kg) | 3275 | 3318 |

[a]Provided (per kilogram of Premix) 2,204,585.5 IU Vit A; 440,917 Vit $D_3$; 4,409.2 IU Vit E; 6.7 mg Vit $B_{12}$; 222.2 mg Menadione; 38,553 mg Choline; 5,555 mg Niacin; 3,777.8 mg D-Pantothenic acid 1,222.2 mg Riboflavin; and 411 mg Thiamin provided (% of Premix).

TABLE 2

Chemical Composition and antioxidant vitamins in *R. heudolotii* seed meal fed to growing pigs.

| Item | Meal[n1] |
|---|---|
| Crude protein, % | 31.4 |
| Total lipid, % | 44.7 |
| Saturated fatty acids, % | 13.5 |
| Monounsaturated fatty acids, % | 12.8 |
| Polyunsaturated fatty acids, % | 73.7 |
| Trans fatty acids, % | n.d |
| Vitamin A, IU/100 g | 192 |
| Vitamin E, IU/100 g | 2.41 | n = 2.
[1]Analyzed by Convance Lab Inc. Madison, WI.

TABLE 3

Fatty acids composition in commercial vegetable oil and njangsa oil seed (*Ricinodendron heudelotii*)

| Fatty acid % | linseed[1] | Canola[1] | Soybean[1] | Corn[1] | Sunflower[1] | Peanut[1] | Olive[1] | NOS[2] |
|---|---|---|---|---|---|---|---|---|
| Palmitic (C16:0) | 4.81 | 3.75 | 9.77 | 10.41 | 5.73 | 9.4 | 10.84 | 18.9 |
| Stearic (C18:0) | 3.03 | 1.87 | 4.16 | 2.03 | 4.78 | 2.65 | 3.59 | 15.2 |
| Palmitoleic (C16:1) | nd | 0.21 | 0.06 | nd | 0.03 | 0.06 | 0.92 | 0.16 |
| Oleic (C18:1, cis) | 21.42 | 62.41 | 22.4 | 24.9 | 15.81 | 46.71 | 75.55 | 6.89 |
| Linoleic (C18:2, cis) | 15.18 | 20.12 | 54.47 | 59.83 | 70.93 | 31.06 | 7.01 | 24.9 |
| Alpha linolenic (C18:3) | 54.24 | 8.37 | 7.38 | 1.03 | 0.37 | 0.23 | 0.66 | 0.8 |
| Eicosapentaenoic (C20:5) | nd | nd | nd | nd | nd | nd | nd | 48.6 |
| Docosahexaenoic (C22:6) | nd | nd | nd | nd | nd | nd | nd | 0.7 |

[1]Data provided by Zambiazi et al. (2007).
[2]Njangsa oilseed (*Ricinodendron heudetotii*), [2]Njangsa oilseed (n = 2); Analyzed by Convance Lab, Madision, Wt.

TABLE 4

Essential amino acid composition of njangsa meal[n] and soybean meal[n]

| | [1]Njangsa meal (%) | [2]Soybean meal (%) |
|---|---|---|
| Essential amino acids | | |
| Arginine | 3.5 | 3.17 |
| Histidine | 0.61 | 1.26 |
| Isoleucine | 1.1 | 1.96 |
| Leucine | 1.6 | 3.43 |
| Lysine | 0.7 | 2.76 |
| Methionine | 0.58 | 0.6 |
| Phenylalanine | 1.26 | 2.26 |
| Tryptophan | 0.1 | 0.59 |
| Threonine | 1.05 | 1.76 |
| Non-essential amino-acids | | |
| Alanine | 1.3 | — |
| Aspartic Acid | 2.5 | — |
| Cystine | 0.97 | — |
| Glutamic Acid | 4.21 | — |
| Glycine | 1.4 | — |
| Proline | 1.2 | — |
| Tyrosine | 0.75 | — |
| Serine | 1.5 | — | n = 2.
[1]Analyzed by Midwest Lab, Omaha, NE.
[2]Cromwell et al, (1999). Journal of Animal Science.

TABLE 5

Growth and carcass traits of finishing hogs supplemented with novel feed additive *Ricinodendron heudelotii* (njangsa)[1]

| Trait | Treatment | Control | Treatment vs. control (P-values)* |
|---|---|---|---|
| Start weight (kg) | 67.38 ± 7.9 | 68.53 ± 6.0 | 0.75 |
| End weight (kg) | 110.75 ± 18.2 | 111.36 ± 110 | 0.93 |
| Average daily gain (kg) | 1.0 ± 0.3 | 0.99 ± 0.1 | 0.91 |
| Slaughter weight (kg) | 104.21 ± 17.9 | 102.22 ± 9.9 | 0.79 |
| Dressing (%) | 75.51 ± 9.2 | 81.08 ± 1.1 | 0.19 |
| Cold carcass weight (kg) | 79.72 ± 14.7 | 80.20 ± 7.4 | 0.97 |
| Moisture loss (%) | 3.13 ± 0.3 | 3.23 ± 0.3 | 0.66 |
| Fat depth (cm) | 1.68 ± 0.1 | 2.44 ± 0.05 | 0.05 |
| Loin eye area (cm$^2$) | 68.65 ± 0.45 | 88.49 ± 0.2 | 0.97 |
| Liver (kg) | 64.56 ± 0.3 | 64.07 ± 0.2 | 0.92 |
| Kidney (kg) | 0.29 ± 0.03 | 0.24 ± 0.02 | 0.008 |
| Heart (kg) | 0.41 ± 0.05 | 0.38 ± 0.02 | 0.27 |

[1]Means ± SD. for 8 animals.
*Significant if P < 0.05

TABLE 6

Effect of long-term (3 years) storage of gastrocnemius muscle of pigs fed R. heudelotii on Vitamins A and E[1] level.

| Item (mg/100 g) | Treatment | |
|---|---|---|
| | Contral | Njangsa |
| Vitamin A | 3.2 ± 1.4[a] | 6.0 ± 1.5[b] |
| Vitamin E | 326.4 ± 107.9[a] | 360.0 ± 187.8[a] |

[a,b]Means within each row with different superscript differ ($P < 0.05$).

REFERENCES

Anigbogu N M (1996). Nature's gifts improving trees and shrubs around the world: R. heudelotii in Nigeria. Agroforestry Today 8(2):18.

AOAC (1995). Official methods of analysis of AOAC International. 16th Ed. Vol. 1 Agricultural Chemicals, Contaminants Drugs, Arlington, Va.

Besong S A, Ezekwe M O, Ezekwe E (2011). Evaluating the effects of freeze-dried supplement at purslane (Portulaca oleracea) on blood lipids in hypercholesterolemic adults. Int. J. Nutr. Metab. 3:43-49.

Cromwell G L, Calvert C C, Cline T R, Crenshaw J D, Crenshaw T D, Easter R A, Ewan R C, Ewan C C, Hamilton C R, Hill G M, Lewis A J, Mahan D C, Miller E R, Nelssen J L, Pettigrew J E, Tribble L F, Veum T L, Yen J T (1999). Variability among sources and laboratories in nutrient analyses of corn and soybean meal. NCR-42 Committee on Swine Nutrition. J. Anim. Sci. 77:3262-3273.

Doran O, Moule S K, Teye G A, Whittington F M, Hallet K G, Wood J D (2006). A reduced protein diet induces stearoyl-co a desaturase protein expression in pig muscle but not in subcutanous adipose tissue: relationship with intra muscular lipid formation. Br. J. Nutr. 95:609-617.

Ekam V S (2003). Evaluation and characterization of the seed oil of Trichosanthes cucumenina (SNA). Glob. J. Pure Appl. Sci. 9:217-220

Flachs P, Horakova O, Brauner P, Rossmeisl M, Pecina P, Franssen-van Hal N, Ruzickova J, Sponarova J, Drahota Z, Vicek C, Keijer J, Houstek J, Kopecky J (2005). Polyunsaturated fatty acids of marine origin unregulated mitochondrial biogenesis and induce beta-oxidation in white fat. Diabetologa 48:2265-237.

ICRAF (1999). Ricinodendron heudelotii. Nairobi ICRAF.

Kopecky J, Rossmeisl M, Brauner P, Jilkova Z, Stankova B, Tvrzicka E, Bryhn M (2009). N-3 PUFA: bioavailability and modulation of adipose tissue function. Proc. Nutr. Soc. 68:361-369.

Manga T T, Foundoun J M, Kengue J, Thiengang C (2000). Chemical composition of R. heudelotii an indigenous fruit tree in Southern Cameroon. Afr. Crop Sci. J. 8:195-201.

Mori T A, Bao D Q, Burke V, Puddey I B, Beilin L J (1999). Docosahexaenoic acid but not eicosapentaenoic acid lowers ambulatory blood pressure and heart rate in humans. Hypertension 34:253-260.

Nettleton J A D (1995). Omega-3 fatty acids and health. Chapman & Hall, N.Y. A Thomson Publishing Co., NY.

Ngo Mpeck M L, Assah E, Tchoundjeu Z, Attangana A R (2003). Strategies for the domestication of R. heudelotii: Evaluation of variability in natural populations from Cameroon. Food Agric. Environ. 3-4:257-262.

NRC (1998). Nutrient requirements of swine, 9th Ed. Washington, D.C., National Research Council. National Academic Press. Washington, D.C. p 189.

Orwa C, Muta A, Kindt R, Jamnatdass, Anthony S (2009). Agroforestry Database: A tree reference and selection guide. 4.0 http://www.worldagroforestry.org/sites/treedb-sltreedatabases.asp.Pa kala R, Lu Sheng W, Benedict C R (1999). Eiosapentaenoic acid and docosahexaenoic acid block serotonin-induced smooth muscle cell proliferation. Arterioscler. Thromb. Vasc. Biol. 19:2316-2322.

Plenderleith K (1997). Ricinodendron heudelotii, a state of knowledge study undertaken for the central Africa regional program for the environment. Oxford Forestry Institute, United Kingdom.

Ruzickova J, Rossmeisl M, Prazak T (2004). Omega-3 PUFA of marine origin limit diet-induced obesity in Mice by reducing cellularity of adipose tissue. Lipids 39:1177-1185.

Stewart J W, Kaplan M L, Beitz D C (2001). Pork with high content of PUFA lowers LDL-cholesterol in women. Am. J. Clin. Nutr. 4:179-187.

Sukhija P S, Palmquist D L (1988). Rapid method for determination of total fatty acid content and composition of feedstuff and feces. J. Agric. Food Chem. 36:1202-1203.

Tchiegang C, Kapseu C, Ndjouenken R, Ngassoum M B (1997). Ricinodendron heudelotii (bail) Kernels: A novel ingredient for tropical agro. J. Food Eng. 32:1-10.

Zambiazi R C, Przybylski R, Zambiazi M W, Mendonça CB (2007). Fatty acid composition of vegetable oils and Fats. B.CEPPA, Curitiba. 25(1):111-120.

What is claimed is:

1. A method of reducing fat in an animal in need thereof, the method comprising:
   forming an oral feed composition comprising a delivery media and at least about percent by weight of Ricinodendron heudelotii (njangsa) seeds, and
   feeding the animal an effective amount of the feed composition for a suitable period of time to reduce fat in the animal,
   wherein the feed composition is metabolized by the animal and the body composition of the animal is improved such that fat is reduced by about 31%; and
   wherein the njangsa seeds are obtained from mature njangsa tree fruit and the seeds are extracted from the seed shells by heating the seed kernels at a temperature above about 100° C.

2. The method of claim 1, wherein an effective amount of said feed composition comprises at least about 2 percent by weight of njangsa seeds fed to said animal for at least about 6 weeks.

3. The method of claim 2, wherein the said feed composition is fed to said animal ad libitum for at least about 6 weeks.

4. The method of claim 1, wherein the animal fat reduction is back fat reduction.

5. The method of claim 1, wherein the delivery media is an orally ingestible solid, liquid, or a combination thereof.

6. The method of claim 1, wherein said feed composition further comprises at least about 14 percent crude protein.

7. The method of claim 1, wherein said feed composition is in the form of a pressed tablet, tablet, paste, powder, pill, gel, encapsulated capsule, liquid, suspension, or a combination thereof.

8. The method of claim 1, wherein said feed composition is in the form of a dietary supplement.

9. The method of claim 1, wherein the njangsa seeds are dried, lyophilized, ground, and mixed with meal diet.

10. The method of claim 1, wherein the njangsa seeds comprise at least one compound selected from the group consisting of proteins, lipids, omega-3 fatty acids, long chain polyunsaturated fats, amino acids, minerals, antioxidants, vitamin A, and vitamin E.

11. A method of reducing fat in an animal in need thereof, the method comprising:
 firming an oral feed composition comprising a delivery media and at least about 2 percent by weight of *Ricinodendron heudelotii* (njangsa) seed extract of njangsa seeds,
 wherein the njangsa seed extract is dried, lyophilized, ground, and mixed with meal diet, and
 feeding the animal an effective amount of the feed composition for a suitable period of time to reduce fat in the animal,
 wherein the feed composition is metabolized by the animal and the body composition of the animal is improved such that fat is reduced by about 31%; and
 wherein the njangsa seeds are obtained from mature njangsa tree fruit and the seeds are extracted from the seed shells by heating the seed kernels at a temperature above about 100° C.

12. The method of claim 11, wherein the njangsa seed extract comprises at least one compound selected from the group consisting of proteins, lipids, omega-3 fatty acids, long chain polyunsaturated fats, amino acids, minerals, antioxidants, vitamin A, and vitamin B.

13. The method of claim 11, wherein the delivery media is an orally ingestible solid, liquid, or a combination thereof.

14. A method of reducing fat and increasing kidney size in an animal in need thereof, and thereby reducing the risks of cardiovascular disease in the animal, the method comprising:
 forming an oral feed composition comprising a delivery media and at least about 2 percent by weight of *Ricinodendron heudelotii* (njangsa) seeds, njangsa seed extract of njangsa seeds, or a combination thereof,
 wherein the njangsa seeds, njangsa seed extract, or the combination thereof is dried, lyophilized, ground, and mixed with meal diet, and
 feeding the animal an effective amount of the feed composition for a suitable period of time to reduce fat and increase kidney size in the animal,
 wherein the feed composition is metabolized by the animal and the body composition of the animal is improved such that fat is reduced by about 31% and kidney size is increased by about 20%; and
 wherein the njangsa seeds and njangsa seed extract are obtained from mature njangsa tree fruit and the seeds are extracted from the seed shells by heating the seed kernels at a temperature above about 100° C.

* * * * *